(12) United States Patent
Burkholz et al.

(10) Patent No.: US 12,343,145 B2
(45) Date of Patent: Jul. 1, 2025

(54) EXTENSION SET AND RELATED SYSTEMS AND METHODS

(71) Applicant: Becton, Dickinson and Company, Franklin Lakes, NJ (US)

(72) Inventors: Jonathan Karl Burkholz, Salt Lake City, UT (US); Megan Scherich, Salt Lake City, UT (US); Yiping Ma, Layton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 613 days.

(21) Appl. No.: 17/192,815

(22) Filed: Mar. 4, 2021

(65) Prior Publication Data
US 2021/0290126 A1 Sep. 23, 2021

Related U.S. Application Data

(60) Provisional application No. 62/993,529, filed on Mar. 23, 2020.

(51) Int. Cl.
*A61B 5/15* (2006.01)
*A61M 25/00* (2006.01)
*A61M 39/10* (2006.01)

(52) U.S. Cl.
CPC ... *A61B 5/150992* (2013.01); *A61M 25/0023* (2013.01); *A61M 25/0082* (2013.01); *A61M 39/10* (2013.01); *A61M 2025/0024* (2013.01)

(58) Field of Classification Search
CPC .......... A61M 25/0023; A61M 25/0082; A61M 25/0113; A61M 39/10; A61M 2025/0024; A61M 2039/1077; A61B 5/150992
See application file for complete search history.

(56) References Cited

U.S. PATENT DOCUMENTS

| 2008/0147011 A1 | 6/2008 | Urmey |
| 2009/0188531 A1* | 7/2009 | Boyle, Jr .............. B08B 9/0436 |
| | | 134/146 |

(Continued)

FOREIGN PATENT DOCUMENTS

| DE | 3140915 A1 | 5/1982 |
| JP | 2010526591 A | 8/2010 |
| WO | 2018/152059 | 8/2018 |

OTHER PUBLICATIONS

Scherich, et al., Flush Instrument with Blood Exposure Protection and Related Methods, U.S. Appl. No. 17/127,588, filed Dec. 18, 2020.

(Continued)

*Primary Examiner* — Bhisma Mehta
*Assistant Examiner* — Haden Matthew Ritchie
(74) *Attorney, Agent, or Firm* — The Webb Law Firm

(57) ABSTRACT

An extension set may include a tube having an outer surface. An instrument, such as a tubing or a probe, may be disposed within the tube and may include a proximal end and a distal end. A translation handle may be coupled to the outer surface of the tube and may move along the outer surface between a proximal position and a distal position to translate the distal end of the instrument between a retracted position and an advanced position. In the advanced position, the distal end of the instrument may extend beyond the distal end of the tube and into a catheter assembly and/or vasculature of a patient.

20 Claims, 8 Drawing Sheets

(56) References Cited

U.S. PATENT DOCUMENTS

| | | | |
|---|---|---|---|
| 2017/0014062 A1* | 1/2017 | Mao | A61B 5/150664 |
| 2017/0056639 A1* | 3/2017 | Ma | A61M 25/002 |
| 2017/0216564 A1* | 8/2017 | Devgon | A61B 5/150816 |
| 2018/0116843 A1* | 5/2018 | Schreck | A61F 2/86 |
| 2019/0021640 A1* | 1/2019 | Burkholz | A61M 25/0637 |
| 2019/0321590 A1 | 10/2019 | Burkholz et al. | |

OTHER PUBLICATIONS

Burkholz, et al., Multi-lumen Extension System, U.S. Appl. No. 17/127,623, filed Dec. 18, 2020.

* cited by examiner

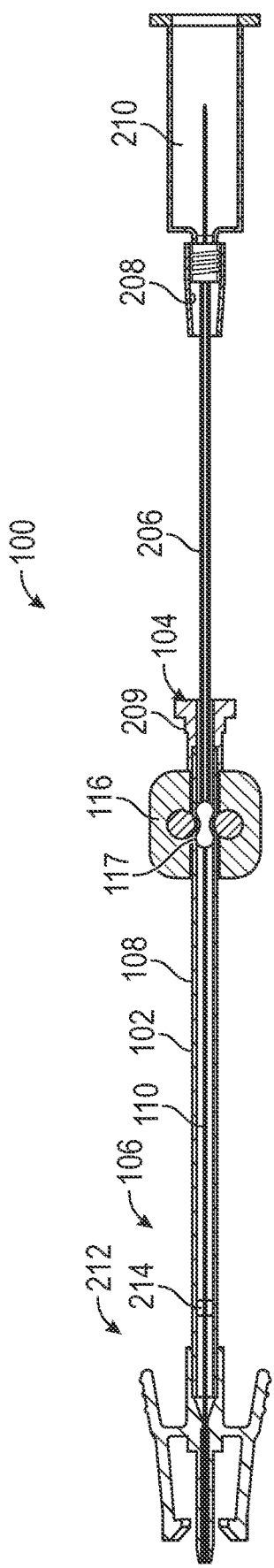
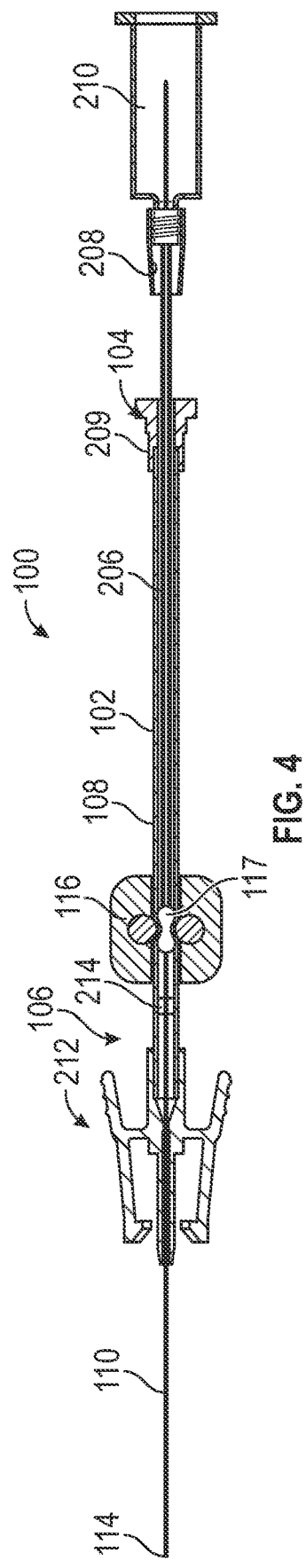

EXTENSION SET AND RELATED SYSTEMS AND METHODS

RELATED APPLICATIONS

This application claims the benefit of U.S. Provisional Patent Application No. 62/993,529, filed on Mar. 23, 2020, entitled "EXTENSION SET AND RELATED SYSTEMS AND METHODS," which is incorporated herein in its entirety.

BACKGROUND

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient to obtain a blood sample.

A common type of catheter is an over-the-needle peripheral intravenous ("IV") catheter. As its name implies, the over-the-needle catheter may be mounted over an introducer needle having a sharp distal tip. The catheter and the introducer needle may be assembled so that the distal tip of the introducer needle extends beyond the distal tip of the catheter with the bevel of the needle facing up away from skin of the patient. The catheter and introducer needle are generally inserted at a shallow angle through the skin into vasculature of the patient.

In order to verify proper placement of the introducer needle and/or the catheter in the blood vessel, a clinician generally confirms that there is "flashback" of blood in a flashback chamber of the catheter assembly. Once placement of the needle has been confirmed, the clinician may temporarily occlude flow in the vasculature and remove the needle, leaving the catheter in place for future blood withdrawal, fluid infusion, or probe access.

Blood withdrawal or infusion using the catheter may be difficult for several reasons, particularly when a dwelling time of the catheter within the patient is more than one day. For example, when the catheter is left inserted in the patient for a prolonged period of time, the catheter may be more susceptible to narrowing, collapse, kinking, blockage by debris (e.g., fibrin or platelet clots), and adhering of a tip of the catheter to the vasculature. Due to this, catheters may often be used for acquiring a blood sample at a time of catheter placement but are much less frequently used for acquiring a blood sample during the catheter dwell period. Therefore, when a blood sample is desired, an additional needle stick is used to provide vein access for blood collection, which may be painful for the patient and result in higher material costs.

The subject matter claimed herein is not limited to embodiments that solve any disadvantages or that operate only in environments such as those described above. Rather, this background is only provided to illustrate one example technology area where some implementations described herein may be practiced.

BRIEF SUMMARY

The present disclosure relates generally to an extension set including a tube that may house an instrument such as a probe or a tubing, for example. The instrument may access a patient's vascular system for medication and fluid delivery and/or blood acquisition during a dwell time of a vascular access device, such as a catheter assembly. In some embodiments, the instrument may access a fluid pathway of the catheter assembly. In other embodiments, the instrument may extend through the catheter assembly to access the vasculature of a patient.

In some embodiments, the extension set may include a tube, which may include a proximal end, a distal end, and an outer surface. In some embodiments, an instrument, such as the probe or the tubing, may be disposed within the tube and may include a proximal end and a distal end. In some embodiments, the tube may shield the instrument from contaminants and/or isolate any blood or other fluids that may remain on the instrument after accessing the fluid pathway of the catheter assembly. In some embodiments, the tube may protect the instrument from a surrounding external environment.

In some embodiments, a translation handle may be coupled to the outer surface of the tube. In some embodiments, the translation handle may move along the outer surface between a proximal position and a distal position. In some embodiments, the translation handle may thus translate the distal end of the instrument between a retracted position and an advanced position. In some embodiments, in the advanced position, the distal end of the instrument may extend beyond the distal end of the tube.

In some embodiments, a fluid path assembly may include the instrument, a proximal end, and a distal end. In some embodiments, an extension tube may be coupled to the proximal end of the instrument. In some embodiments, the proximal end of the fluid path assembly may include a proximal connector configured to connect to a blood collection device. In some embodiments, the fluid path assembly may extend through the tube.

In some embodiments, the distal end of the tube may include a distal connector. In some embodiments, the distal end of the tube and/or the distal connector may include a fluid seal to seal the tube and create a closed fluid path.

In some embodiments, the instrument may extend distally from a coupler element to facilitate translating the instrument within the tube without requiring direct contact. In some embodiments, the extension tube may be coupled to the instrument via the coupler element. In some embodiments, the tube may be axially-compressible such that the translation handle compresses a portion of the tube between the coupler element and the translation handle. In some embodiments, the compressed portion of the tube may engage with the coupler element such that movement of the translation handle along the outer surface of the tube translates the distal end of the instrument between the retracted position and the distal position.

In some embodiments, the coupler element and/or the tube may include a lubricant to facilitate translation of the instrument within the tube. In these and other embodiments, the translation handle may include a roller and/or bearing to provide localized compression of the tube to engage the coupler element through the tube.

In some embodiments, the instrument may be disposed within the tube and may include a proximal end and a distal end. In some embodiments, in response to the translation handle moving to the distal end of the tube, the distal end of the instrument may extend beyond the distal end of the tube.

In some embodiments, a method to provide access to a patient's vascular system may include coupling the extension set to a catheter assembly. In some embodiments, the extension set may include the tube, an instrument disposed within the tube, and the translation handle coupled to the outer surface of the tube. In some embodiments, coupling the extension set to the catheter assembly may include coupling the distal end of the tube to the catheter assembly. In some embodiments, the method may further include moving the translation handle along the tube from the proximal position to the distal position. In some embodiments, in the distal position, the distal end of the instrument may extend beyond the distal end of the tube into the catheter assembly.

In some embodiments, coupling the distal end of the tube to the catheter assembly may include coupling the distal connector of the tube to the catheter assembly. In some embodiments, the catheter assembly may include a catheter extending from a distal end thereof. In some embodiments, in response to the translation handle moving to the distal position, the instrument may extend through a distal end of the catheter.

In some embodiments, the extension set may include the blood collection device. In some embodiments, after blood has been collected in the blood collection device, the method may include moving the translation handle from the distal position to the proximal position. In some embodiments, moving the translation handle to the proximal position may retract the distal end of the instrument into the tube.

It is to be understood that both the foregoing general description and the following detailed description are examples and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which:

FIG. 3 is a partial cutaway view of the extension set, illustrating the instrument in a retracted position according to some embodiments;

FIG. 4 is a partial cutaway view of the extension set, illustrating the instrument in an advanced position according to some embodiments;

DETAILED DESCRIPTION

As used herein, the terms "proximal" and "distal" may refer to the direction closer to and away from, respectively, a clinician who would place the catheter system into contact with a patient. Thus, for example, the end of the catheter system first touching the body of the patient would be the distal end, while the opposite end of the catheter system would be the proximal end of the catheter system.

An extension set in accordance with some embodiments may provide access to a patient's vascular system. As discussed in more detail below, in some embodiments, the extension set may provide access to a fluid pathway of a catheter assembly. In some embodiments, the extension set may provide access to the vasculature of a patient throughout a dwell time of the catheter assembly for medication and fluid delivery and/or blood draw.

As previously mentioned, a catheter with significant dwell time within the vasculature of the patient may be susceptible to narrowing, collapse, kinking, blockage by debris (e.g., fibrin or platelet clots), and adhering of a tip of the catheter to vasculature of a patient. Thus, blood withdrawal using the catheter may be difficult. Advantageously, in some embodiments, the extension set may include an instrument, such as another catheter or a probe, disposed within a tube. In some embodiments, the instrument may provide access to the vasculature of the patient without any additional needle sticks. Thus, in some embodiments, the extension set 100 may be used for needle-free blood collection and/or fluid infusion.

Figure 1:
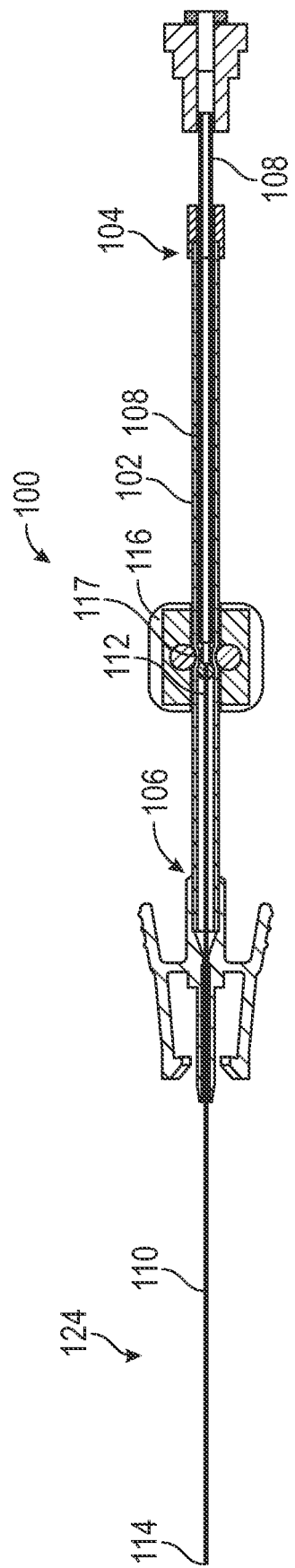
FIG. 1 is an upper perspective view of an example extension set, illustrating an example instrument in an advanced position, according to some embodiments.

Referring now to FIG. 1, in some embodiments, the extension set 100 may include the tube 102, which may include a proximal end 104, a distal end 106, and an outer surface 108. In some embodiments, the tube 102 may be flexible, rigid, or semi-rigid. In some embodiments, the instrument 110 may be disposed within the tube 102 and may include a proximal end 112 and a distal end 114. The distal end 114 may be atraumatic or blunt in some embodiments. In some embodiments, the extension set 100 may provide a non-fluid path through the tube 102 to shield the instrument 110 from contaminants and the surrounding external environment. The non-fluid path may be configured such that blood withdrawn from the patient does not contact the non-fluid path. In some embodiments, the extension set 100 may also isolate blood or other fluids that may remain on the instrument 110 after use. Further, in some embodiments, the extension set 100 may provide support, alignment, and aseptic delivery of the instrument 110 through the catheter assembly and into the patient's vascular system.

In some embodiments, a translation handle 116 may be coupled to the outer surface 108 of the tube 102 to facilitate moving the instrument 110 without requiring direct contact with the instrument 110. In some embodiments, the translation handle 116 may move along a length of the outer surface 108 of the tube 102 between a proximal position and a distal position. In some embodiments, the tube 102 may include an axially-compressible, bio-compatible, and an elastomeric or polymeric material. In this manner, in some embodiments, the translation handle 116 may create localized compression of the tube 102.

As discussed in more detail below, in some embodiments, a compressed portion of the tube 102 may engage with a coupler element 117 coupled to the proximal end 112 of the instrument 110 such that the translation handle 116 may translate the distal end 114 of the instrument 110 in the direction of movement of the translation handle 116. In some embodiments, the translation handle 116 may translate the distal end 114 of the instrument 110 between a retracted position and an advanced position. In the advanced position 124, as illustrated in FIG. 1, the distal end 114 of the instrument 110 may extend beyond the distal end 106 of the tube 102 and into a catheter assembly or vasculature of a patient, for example.

Figure 2:
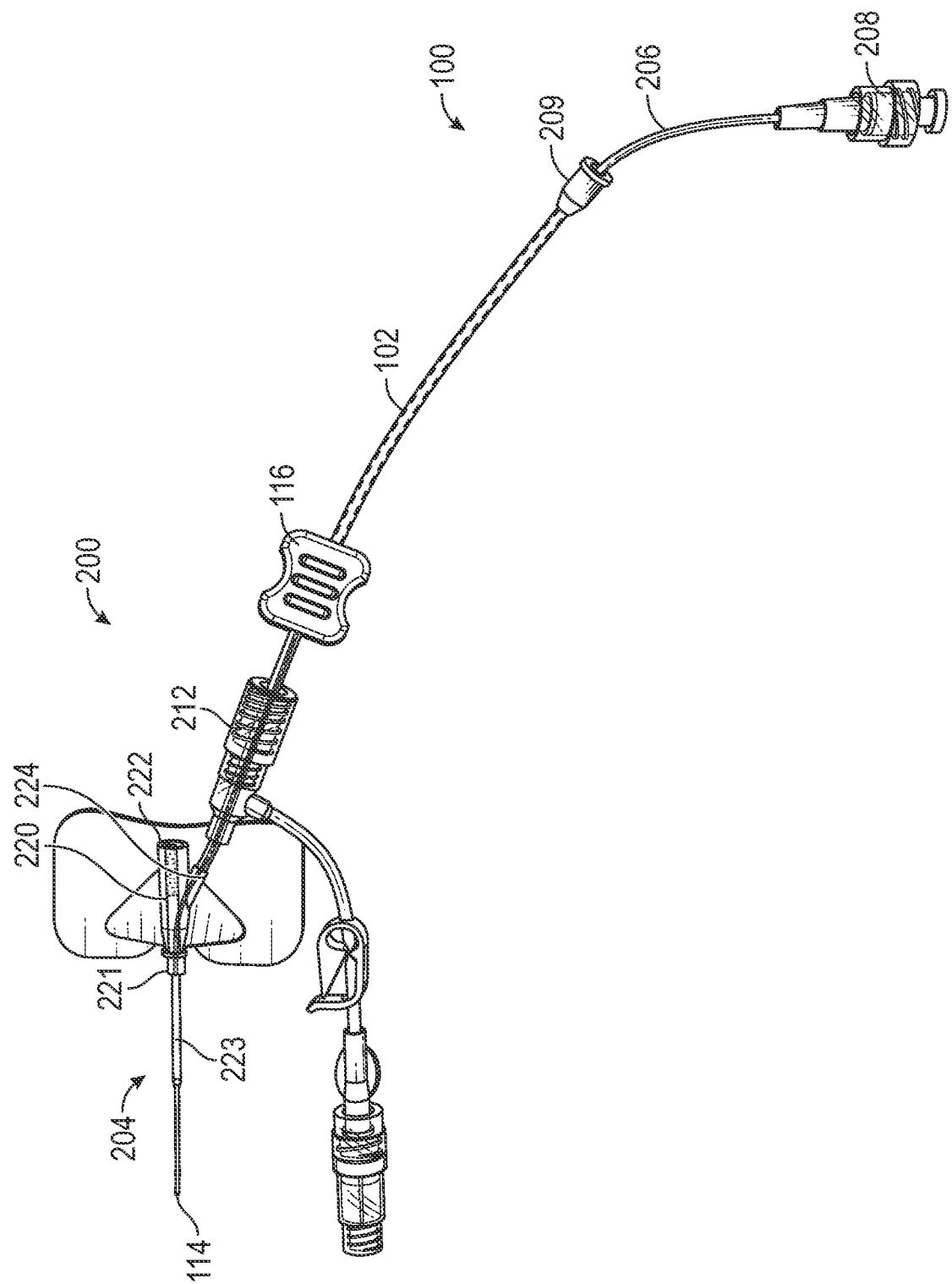
FIG. 2 is an upper perspective view of the extension set coupled to an example catheter assembly, according to some embodiments.

Referring now to FIG. 2, in some embodiments, the extension set 100 may be coupled to a catheter assembly 200, which may include a distal end 204. In some embodiments, the instrument 110 may extend through the distal end 204 of the catheter assembly 200 in response to the translation handle 116 moving to the distal position.

In some embodiments, the instrument 110 may include a probe having one or more openings and/or sensors to provide in-vein patient and device monitoring. In some embodiments, the probe openings and/or the sensors may be disposed towards the distal end 114. In some embodiments, the openings may serve as fluid inlets and/or outlets. In some embodiments, the sensors may measure one or more parameters and/or detect one or more elements related to, for example, diagnostic information, blood chemistry, pH, temperature, pressure, flow rate, drug identification, microbes, placement of an implantable stent, in-vein catheter tip stabilization feature, or other devices or physiological measures. In some embodiments, the extension set 100 may facilitate placement of a portion of the probe that includes the sensors within the fluid pathway of the catheter assembly and/or the vasculature of the patient.

In some embodiments, the instrument 110 may include tubing and may function as both a probe and a catheter, including elements of both. In some embodiments, the instrument 110 may include the tubing to provide fluid infusion and/or withdrawal. In some embodiments, the tubing may include a standard catheter tip or an asymmetrical catheter tip. In some embodiments, diffuser holes may be disposed in a tip of the tubing. In some embodiments, the tubing may include polyurethane, FEP, Teflon, silicon, TPE, TPU, fluorinated polymers, polyimide, or any other suitable materials or combination thereof. In some embodiments, the tubing material may be hydrophilic, hydrophobic, and/or may include any other desired properties or features, such as an anti-fouling material. Some embodiments of the tubing may include a coating such as an anti-thrombogenic coating or other coating to impart other desired properties to the tubing.

In some embodiments, an extension tube 206 may be coupled to a proximal end of the translation handle 116 and/or the proximal end 112 of the instrument 110. In some embodiments, the extension tube 206 may be flexible. In some embodiments, the extension tube 206 may include TPE, TPU, PVC, or other suitable medical tubing material. In some embodiments, the extension tube 206 may be substantially clear and/or may include markers to inform a clinician of the position of the instrument 110 relative to the catheter or catheter features. In some embodiments, the extension tube 206 may include a textured surface to reduce contact friction. Some embodiments of the extension tube 206 may be vented by, for example, an open air pathway, a breathable filter membrane, porous venting material, microchannels, or the like.

In some embodiments, a proximal connector 208 may coupled to or integrated with the proximal end of the extension tube 206 to connect to a blood collection device 210 (see, for example, FIG. 3), infusion device, or monitoring device, for example. In some embodiments, the blood collection device may include any suitable blood collection device, such as, for example, a VACUTAINER® or a VACUTAINER® LUER-LOK™, available from Becton Dickinson and Company of Franklin Lakes, New Jersey. The proximal connector 208 may include, for example, a male or female luer, a blunt cannula, or another suitable connector.

In some embodiments, the distal end 106 of the tube 102 may be coupled to or integrated with the distal connector 212, which may include a fluid seal 214 to seal the tube 102 and create a closed fluid path. In some embodiments, the distal connector 212 may include, for example, a male or female luer, a blunt cannula, or another suitable connector.

In some embodiments, the extension tube 206 may extend through a proximal connector 209 integrated with or coupled to the proximal end 104 of the tube 102. In some embodiments, there may be a tight fit or septum between the extension tube 206 and the proximal connector 209, which may create a seal but still allow motion of the extension tube 206 with respect to the proximal connector 209. In some embodiments, the translation handle 116 may be moved from the proximal position to the distal position such that the distal end 114 of the instrument 110 is distally advanced beyond the tube 102 and/or the proximal connector 208 is moved closer to the proximal connector 209. In some embodiments, after blood has been collected in the blood collection device 210, the translation handle 116 may be moved from the distal position to the proximal position such that the distal end 114 of the instrument 110 retracts into the tube 102 and/or the proximal connector 208 is moved away from the proximal connector 209. In some embodiments, the translation handle 116 may include any suitable translation handle, which may be described, for example, in further detail in U.S. patent application Ser. No. 17/127,588, filed Dec. 18, 2020, entitled "FLUSH INSTRUMENT WITH BLOOD EXPOSURE PROTECTION AND RELATED METHODS" and U.S. patent application Ser. No. 17/127,623, filed Dec. 18, 2020, entitled "MULTI-LUMEN EXTENSION SYSTEM," which are incorporated by reference in their entirety.

In some embodiments, the extension set 100 may reduce hemolysis of a blood sample collected via the fluid path. In some embodiments, the extension set 100 may provide an adequate fluid flow rate. Blood cell experiences shear stress as it flows in a fluid pathway. The maximum shear stress is along the wall of the blood cell, or wall shear stress. Wall shear stress on blood cells is considered a major source of mechanical damage to blood cells. For a cylindrical fluid path, the wall shear stress is typically expressed as:

$$T = \frac{1}{2} \cdot \frac{\Delta p}{L} \cdot (kr)$$

in which $\Delta P$ is the pressure drop along a path with a length of L and an interior radius of r. k is shrinkage index.

To fill a certain volume of collection tube, V, with a flow rate of Q, the time needed can be simply assessed by:

$$t = \frac{v}{Q} = 8\mu v \cdot \frac{1}{\pi r^4} / \left(\frac{\Delta p}{L}\right)$$

in which µ is the dynamic viscosity of the fluid. Hemolysis is typically associated with both the wall shear stress and the time a blood cell is exposed to wall shear stress. From literature, it has been widely considered that hemolysis index can be approached as a function of:

$$HI(\%) = A * t^\alpha * T^\beta$$

in which A, α, and β are coefficients.

In principle, the hemolysis index is related to pressure gradient and cross-sectional characteristic dimension:

$$HI(\%) \propto \left(\frac{\Delta P}{l}\right)^{\beta-\alpha} \cdot \left(\frac{1}{r}\right)^{4\alpha-\beta}$$

In some embodiments, a length of the extension set 100 may be selected based on one or more of the following: a gauge of a particular catheter, a particular catheter assembly configuration, or a clinical setup. In some embodiments, the extension set 100 may include a length L. In some embodiments, the extension set 100 may include an inner diameter D.

Fluid flow in a fluid pathway through the extension set 100 that is tubular can be analyzed using Poiseuille's equation:

$$Q = \frac{\pi D^4 \Delta P}{128 \mu L} = \frac{\Delta P}{R_f}$$

where ΔP is a change in pressure gradient across the length of the fluid pathway, D and L are the inner diameter and length, respectively, of the fluid pathway, µ is the viscosity of a fluid, and $$R_f = \frac{128 \mu L}{\pi D^4}$$

is the fluid resistance. Since µ is the viscosity of the fluid and not part of the extension tube geometry, a geometric factor $G_f$ is defined such that $R_f$ (the fluid resistance) is $$R_f = \frac{128 \mu}{\pi} G_f,$$

where $$G_f = \frac{L}{D^4}.$$

In some embodiments, the fluid pathway through the extension set 100 may have multiple sections with lengths (L1, L2, L3) and inner diameters of (D1, D2, D3), the geometric factor is then:

$$G_f = \frac{L1}{D1^4} + \frac{L2}{D2^4} + \frac{L3}{D3^4}$$

In some embodiments, the fluid pathway through the extension set 100 may have inside diameter that changes over the length of the extension set 100, the geometric factor is then:

$$G_f = \int_0^L \frac{dl}{D(l)^4} \quad (1)$$

In some embodiments, the fluid pathway through the extension set 100 may have a cross section that is not circular or may have a complicated inner diameter profile. The geometric factor can then be determined by measuring the flow rate (Q) at given pressure (ΔP) with known viscosity (µ) fluid:

$$G_f = \frac{\pi \Delta P}{128 \mu Q}$$

The $G_f$ value of the fluid pathway through the extension set 100 may be selected to reduce the maximum shear stress for each catheter gauge to be the same or less than the max shear stress of a BD 21G VACUTAINER® UltraTouch™ push button blood collection set (available from Becton, Dickinson & Company of Franklin Lakes, New Jersey), which was previously considered the gold standard for blood draws. In some embodiments, $G_f$ value of the fluid pathway may be selected to reduce the maximum shear stress for each catheter gauge to be the same or less than the max shear stress of a BD 25G VACUTAINER® UltraTouch™ push button blood collection set (available from Becton, Dickinson & Company of Franklin Lakes, New Jersey).

In some embodiments, a fluid pathway of the blood collection system, which may include one or more of the blood collection device, the extension set 100, and the catheter assembly 200 (which may include an extension tube extending from the side port 224), may include an entirety of a blood collection pathway through which blood flows after leaving the vasculature and into or through the blood collection device during blood collection. The system geometric factor Gr for the fluid pathway of the blood collection system can be determined in similar fashion as the $G_f$ value of the fluid pathway through the extension set 100 as described earlier. In some embodiments, the system geometric factor $G_{fs}$ may be equal to or more than 7.34E+06 (1/in³) when the instrument 110 is in an advanced position. In some embodiments, $G_{fs}$ may include another value. In some embodiments, the system geometric factor $G_{fs}$ may be 7.34E+06 (1/in³) plus or minus 10 percent, plus or minus 25 percent, plus or minus 50 percent, or plus or minus 75 percent. In some embodiments, $G_{fs}$ may include another value, which may be selected based on a gauge and/or length of the catheter 223.

In some embodiments, the distal connector 212 may couple the extension set 100 to the catheter assembly 200. In some embodiments, the catheter assembly 200 may include a catheter adapter 220, which may include a distal end 221, a proximal end 222, and a lumen extending therethrough. In some embodiments, the catheter adapter 220 may include a side port 224, from which another extension tube may extend. In some embodiments, the other extension tube may be coupled to an adapter, such as a Y-adapter or a T-adapter, for example. In some embodiments, the distal end 106 of the tube 102 may be coupled to the proximal end 222 of the catheter adapter 220, the side port 224, the adapter, or another portion of the catheter assembly 200. In some embodiments, the distal end 204 of the catheter assembly 200 may include a catheter 223, which may be secured within the catheter adapter 220 and extend distally from the distal end 221 of the catheter adapter 220. In some embodiments, the catheter 223 may include a peripheral IV catheter, a midline catheter, or a peripherally-inserted central catheter.

In some embodiments, the catheter 223 may include a standard catheter tip or an asymmetrical catheter tip. In some embodiments, the catheter 223 may include one or more diffuser holes may be disposed in a tip of the catheter 223. In some embodiments, the catheter 223 may include polyurethane, FEP, Teflon, silicon, TPE, TPU, fluorinated polymers, polyimide, or any other suitable materials or combination thereof. In some embodiments, the catheter 223 material may be hydrophilic, hydrophobic, and/or may include any other desired properties or features, such as an anti-fouling material. Some embodiments of the catheter 223 may include a coating such as an anti-thrombogenic coating or other coating to impart other desired properties to the catheter 223.

Referring now to FIGS. 3-4, in some embodiments, the fluid seal 214 may permit advancement and/or retraction of the instrument 110 therethrough while maintaining a closed fluid path. In some embodiments, the fluid seal 214 may include silicone rubber, an elastomer, or another suitable material. In some embodiments, the fluid seal 214 may include an aperture, slit, or the like to accommodate the instrument 110 therethrough.

In some embodiments, the compressed portion 302 of the tube 102 may engage with the coupler element 117 such that movement of the translation handle 116 along the outer surface 108 of the tube 102 translates the distal end 114 of the instrument 110 between the retracted position, illustrated in FIG. 3, and the advanced position, illustrated in FIG. 4. In some embodiments, the coupler element 117 may be coupled to the instrument 110 and/or the extension tube 206 by, for example, an interference fit, adhesive, or both. In some embodiments, the extension tube 206 and the instrument 110 may be monolithically formed as a single unit and may extend through the coupler element 117.

Figure 5A:
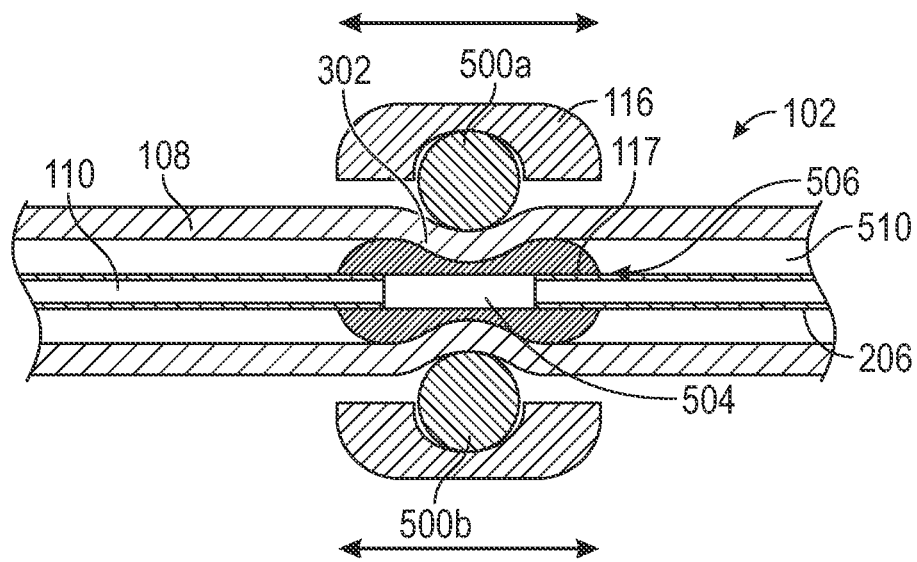
FIG. 5A is a cross-sectional view of an example translation device, according to some embodiments.
Figure 5B:
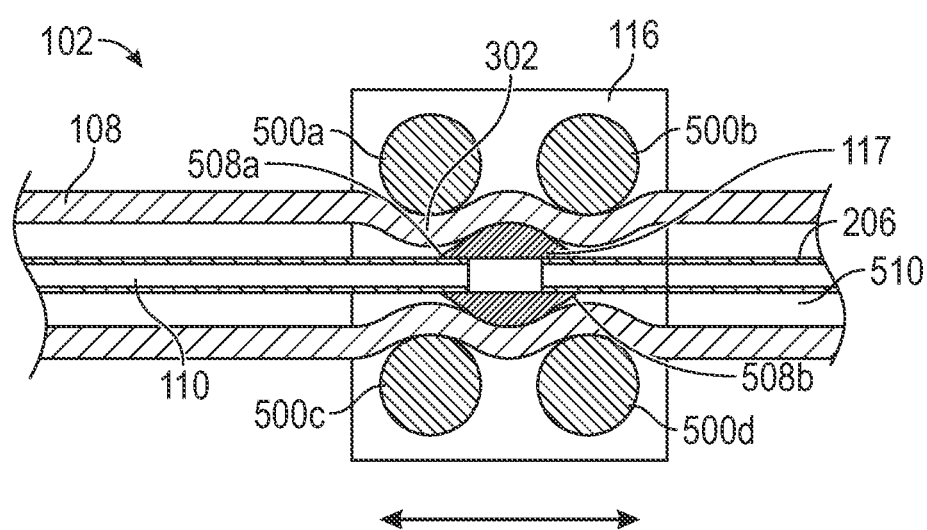
FIG. 5B is a cross-sectional view of another example translation device of the extension set, according to some embodiments.

Referring now to FIGS. 5A and 5B, in some embodiments, the coupler element 117 may engage or otherwise engage with one or more features of the translation handle 116 through the tube 102 to allow translation of the instrument 110 without any direct contact between the translation handle 116 and the coupler element 117 that is coupled to the instrument 110. For example, in some embodiments, as illustrated in FIG. 5A, the coupler element 117 may include a disc or ellipsoid shape 506 with a flattened or concave center portion 504. The flattened or concave center portion 504 may align with opposing features 500 of the translation handle 116 to facilitate smooth translation. In some embodiments, the features 500 may include rollers, ball bearings, low-friction sliding surfaces, or the like. In some embodiments, the features 500 may be rounded, angled, spherical, or cylindrical.

In some embodiments, a distance between features 500 that oppose each other may be less than an outer diameter of the tube 102 such that the tube 102 is pinched between the features 500 and the coupler element 117. In some embodiments, as illustrated in FIG. 5B, the coupler element 117 may include a disc or ellipsoid shape having tapered ends 508. The tapered ends 508 may accommodate the features 500 of the translation handle 116 to facilitate smooth translation.

In some embodiments, the features 500 may be coupled to the translation handle 116 to provide localized compression of the tube 102. In some embodiments, the features 500 may engage with the coupler element 117 via the tube 102 to facilitate smooth translation of the instrument 110 within the tube 102. In some embodiments, the features 500 may be coupled to an interior edge of the translation handle 116. In some embodiments, the surface of the coupler element 117 that interfaces with the features 500 may be substantially concave to facilitate smooth bi-lateral movement along the outer surface 108 of the tube 102.

According to various embodiments, the coupler element 117 may include the tapered ends 508 to improve its ability to round corners during movement between the proximal end 104 and the distal end 106 of the tube 102. In these and other embodiments, the coupler element 117 may include fins to facilitate travel down the tube 102. In some embodiments, the coupler element 117 may include fenestrations, ribs, or channels to facilitate fluid flow, such as air and/or liquid. In some embodiments, air may flow around the coupler element 117 such as through the fenestrations, ribs, or channels, so a vacuum is reduced or eliminated in response to moving the coupler element 117 distally or proximally. In other embodiments, the coupler element 117 may include a bore to accommodate fluid flow, such as fluid infused into the patient's vascular system, for example, or blood aspirated from the patient's vascular system. In some embodiments, the coupler element 117 may include one or more colors or patterns to increase its visibility.

In some embodiments, longitudinal ribs may be molded onto an outer surface of the coupler element 117 to keep the coupler element 117 oriented parallel to the tube 102, thus facilitating unobstructed bi-directional movement of the coupler element 117 through the tube 102. In some embodiments, the longitudinal ribs may contact opposing features on an inner surface of the tube 102 to prevent the coupler element 117 from rotating within the tube 102.

In some embodiments, the coupler element 117 and/or an inner surface of the tube 102 may include a lubricant 304 to facilitate translation of the instrument 110 within the tube 102. In some embodiments, the lubricant 304 may be disposed around the coupler element 117 and/or inside a non-fluid path lumen 510 of the tube 102. In other embodiments, the lubricant 304 may be applied external to the non-fluid path lumen 510 around the features 500 of the translation handle 116. In some embodiments, the coupler element 117 may be include lubricious material to facilitate movement within the non-fluid path lumen 510. In these and other embodiments, the extension set 100 may include venting to maintain atmospheric pressure and allow movement of air within the non-fluid path lumen 510 during bi-directional translation of the instrument 110. In some embodiments, the non-fluid path lumen 510 may include venting to allow airflow into and out of the non-fluid path lumen 510, which may facilitate movement of the translation handle 116 and coupler element 117. In some embodiments, one or more vents to provide the venting may be reduced in size to allow air movement while still maintaining good aseptic protection of the instrument 110 and/or other portions of the extension set 100.

Figure 6:
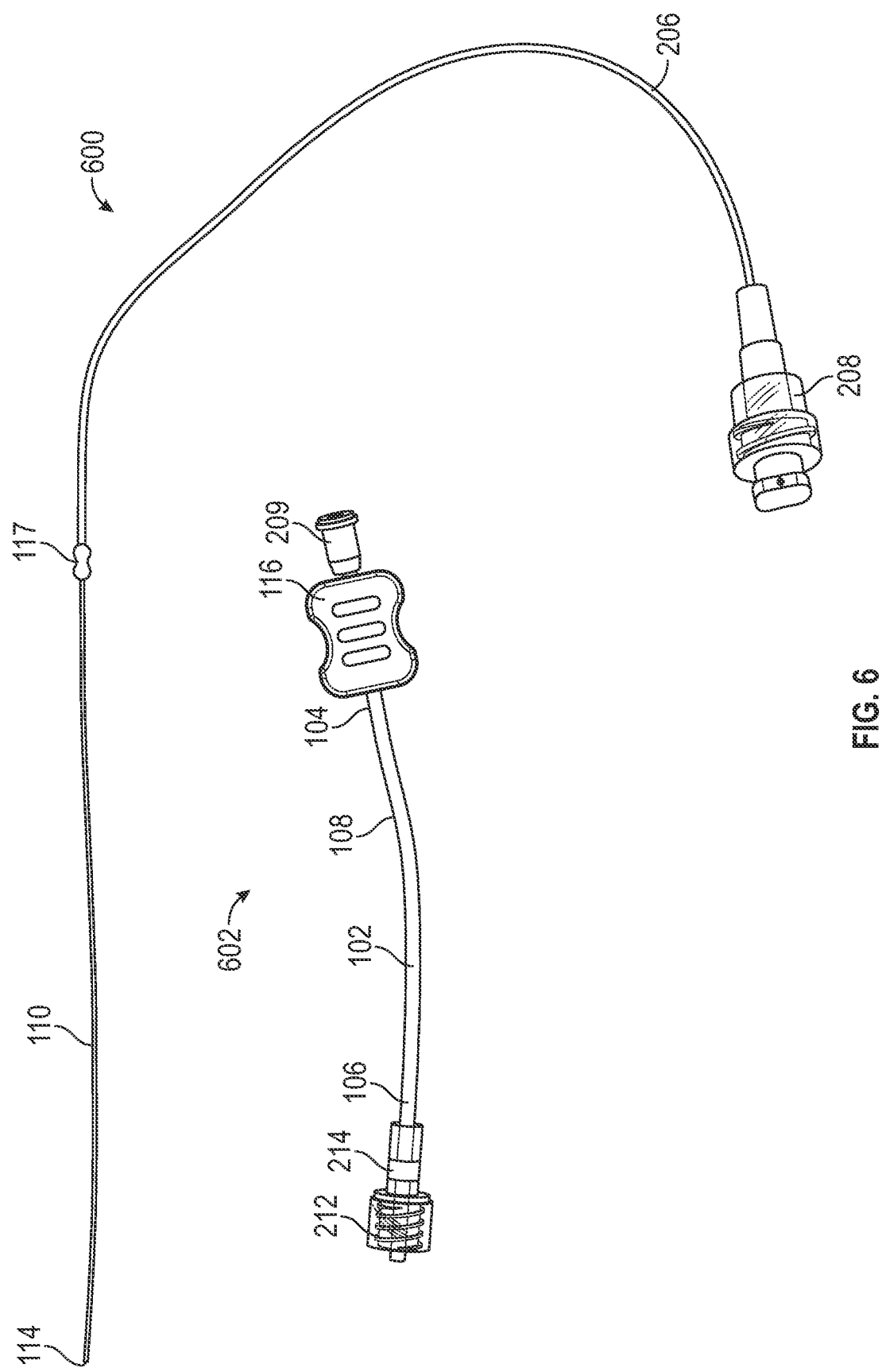
FIG. 6 is a partially exploded view of an example translation device of the extension set, according to some embodiments.
Figure 7:
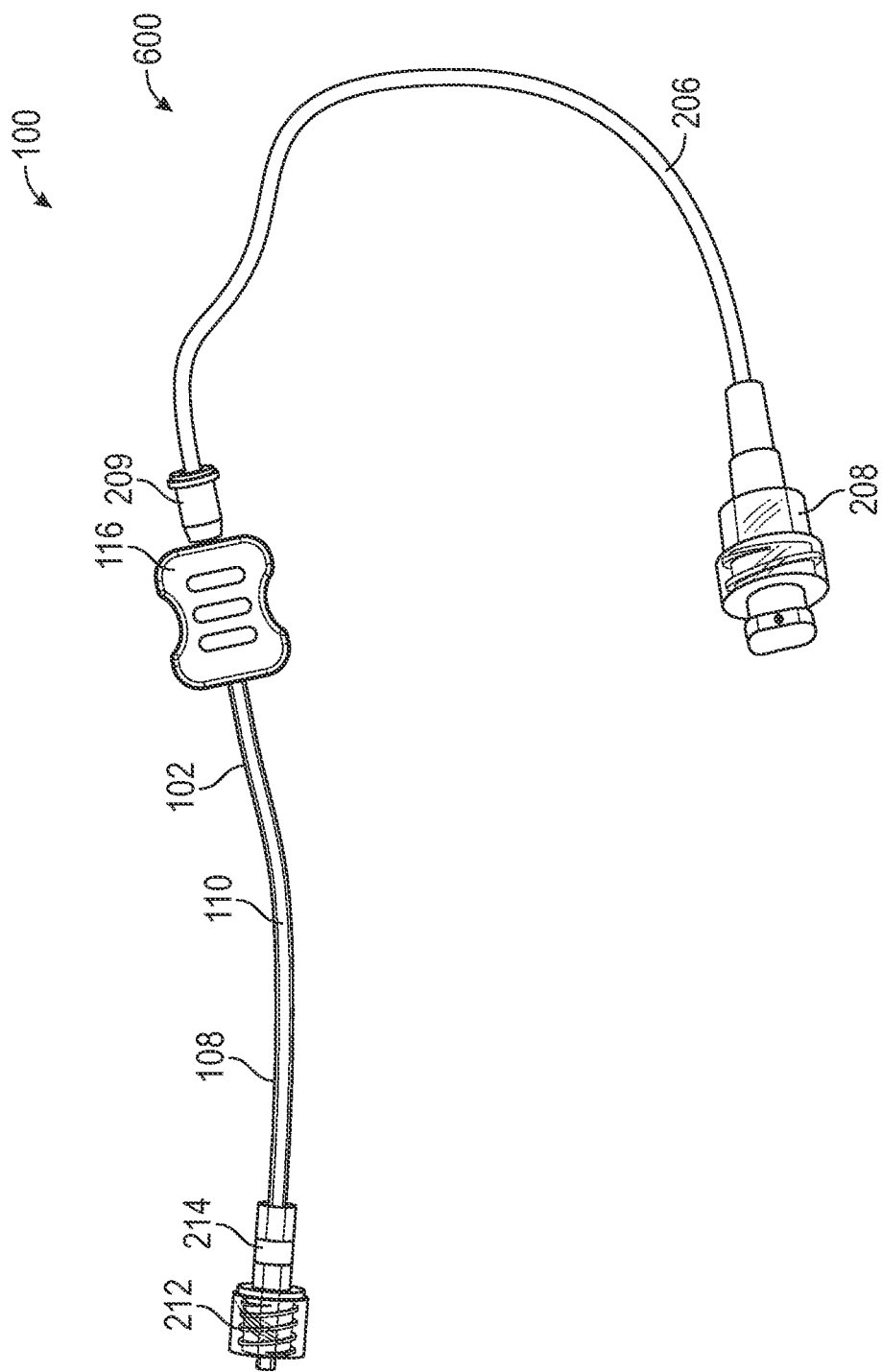
FIG. 7 is an upper perspective view of the extension set, illustrating the instrument in the retracted position according to some embodiments.
Figure 8:
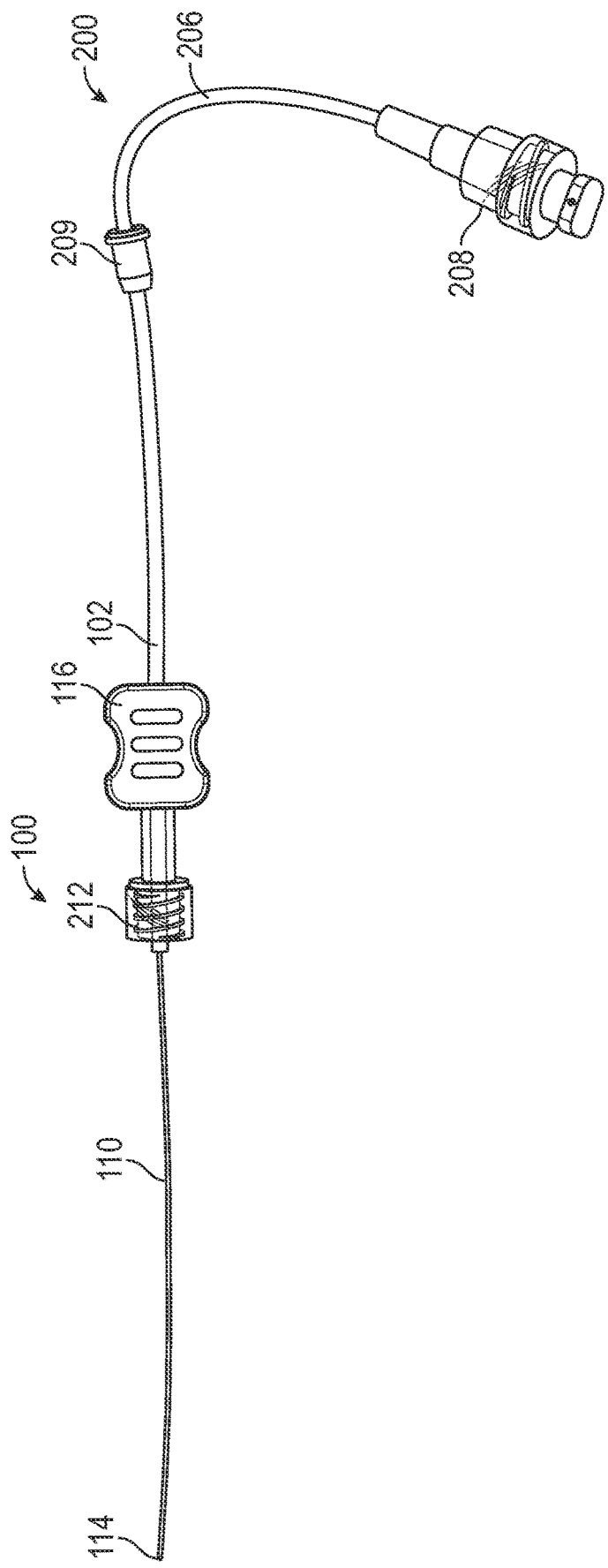
FIG. 8 is an upper perspective view of the extension set, illustrating the instrument in the advanced position, according to some embodiments.

Referring now to FIGS. 6-8, in some embodiments, the extension set 100 and the catheter assembly 200 may include a fluid path assembly 600 that facilitates blood collection. In some embodiments, the fluid path assembly 600 may include the instrument 110, which may include the tubing, such as, for example, micro-tubing. In some embodiments, tubing may include a polymer material, polyimide, or another suitable material. In some embodiments, the proximal connector 208 may be coupled to a needle-less connector or a female luer connector. In some embodiments, blood may flow through the instrument 110 and through the extension tube 206 into the blood collection device.

In some embodiments, a non-fluid path extension assembly 602 may provide support, alignment, and aseptic delivery of the instrument 110 through a catheter (see, for example, the catheter 223 of FIG. 2) dwelling within the vasculature. In some embodiments, a majority of the non-fluid path extension assembly 602 or a portion of the non-fluid path extension assembly 602 proximal to the fluid seal 214 may not contact blood being withdrawn from the patient through the extension set 100. In some embodiments, a portion of the non-fluid path extension assembly distal to the fluid seal 214 may have some contact with blood or saline solution that may be in a fluid path of the catheter. In some embodiments, the non-fluid path extension assembly 602 may include one or more of: the tube 102, the translation handle 116, the distal connector 212 at the distal end 106, and the proximal connector 209 disposed at the proximal end. In some embodiments, the distal end 106 of the tube 102 and/or the distal connector 212 may include the fluid seal 214 to seal the distal end of the non-fluid path extension assembly 602. In some embodiments, the fluid seal 214 may form a seal around the instrument 110, which may extend therethrough. Advantageously, the extension set 100 in accordance with some embodiments may be easy to scale in length, based on, for example, a size or length of the catheter 123 or the catheter assembly 200.

Figure 9A:
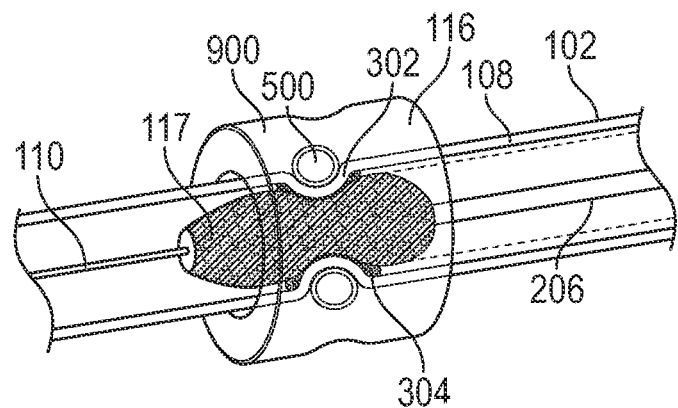
FIG. 9A is an upper perspective view of an example translation handle and example coupler element, according to some embodiments.
Figure 9B:
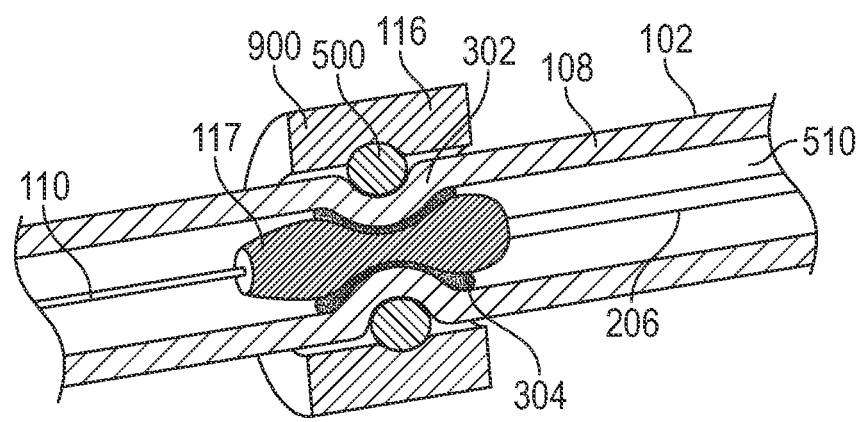
FIG. 9B is a cross-sectional view of the translation handle and the coupler element of FIG. 9A, according to some embodiments.

Referring now to FIGS. 9A and 9B, in some embodiments, the translation handle 116 may include a collar 900 around the tube 102. The tubing 102 is illustrated as transparent in FIG. 9B for illustrative purposes. In some embodiments, the collar 900 may extend fully or partially around the tube 102. In some embodiments, the collar 900 may move bi-directionally along the tube 102. In some embodiments, the collar 900 and the coupler element 117 may be magnetically attracted to each other through the tube 102 to facilitate movement of the instrument 110 without direct contact. These and other embodiments of the collar 900 may include the features 500 to improve ease of movement along the outer surface 108 of the tube 102. In some embodiments, an outer surface of the collar 900 may include one or more grips, such as, for example, ribs, textured surfaces, push tabs, or other protrusions to provide ease of handling.

In some embodiments, the features 500 may include one, two, or three ball bearings distributed radially symmetrically about the longitudinal axis of the tube 102. In some embodiments, the features 500 may be coupled to an inside surface of the collar 900 to mediate contact between the collar 900 and the outer surface 108 of the tube 102. In other embodiments, any number of the features 500 may be present and may be arranged in a variety of symmetrical and asymmetrical arrangements.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the disclosed embodiments.

The invention claimed is:

1. An extension set to provide access to a patient's vascular system, comprising:
a tube, comprising a proximal end, a distal end, and an outer surface;
an instrument disposed within the tube, the instrument comprising a proximal end and a distal end; and
a translation handle coupled to the outer surface of the tube, wherein the translation handle is configured to move along the outer surface of the tube between a proximal position and a distal position to translate the distal end of the instrument between a retracted position and an advanced position, wherein in response to the distal end of the instrument being in the advanced position, the distal end of the instrument extends beyond the distal end of the tube;
wherein the translation handle facilitates movement of the instrument without direct contact between the translation handle and the instrument; and
wherein the instrument comprises a coupler element positioned within the tube, with the translation handle compressing a portion of the tube in between the coupler element and the translation handle in a direction orthogonal to movement of the translation handle, and wherein the portion of the tube engages with the coupler element such that movement of the translation handle along the outer surface of the tube translates the distal end of the instrument between the retracted position and the advanced position.

2. The extension set of claim 1, wherein the instrument comprises a tubing.

3. The extension set of claim 1, further comprising a fluid path assembly comprising the instrument, a proximal end, and a distal end, wherein an extension tube is coupled to the proximal end of the instrument and wherein the proximal end of the fluid path assembly comprises a proximal connector configured to connect to a blood collection device.

4. The extension set of claim 1, wherein the distal end of the tube comprises a distal connector.

5. The extension set of claim 4, wherein the distal end of the tube or the distal connector comprises a fluid seal to seal the tube.

6. The extension set of claim 1, wherein at least one of the coupler element and the tube comprises a lubricant to facilitate translation of the instrument within the tube.

7. The extension set of claim 1, wherein the translation handle comprises features formed thereon on opposing sides of the tube, the features comprising one of rollers, ball bearings, or low-friction sliding surfaces;
wherein the coupler element comprises a disc or ellipsoid shape with a flattened or concave center portion; and
wherein the flattened or concave center portion longitudinally aligns with the features to facilitate engagement of the features with the coupler element through the tube and smooth translation of the translation handle.

8. The extension set of claim 7, wherein a distance between the features opposing sides of the tube is less than an outer diameter of the tube, such that the tube is pinched between the features and the coupler element.

9. An extension set to provide access to a patient's vascular system, comprising:
a fluid path assembly comprising an instrument, an extension tube, and a proximal connector configured to couple to a blood collection set;
a tube comprising a proximal end, a distal end, and an outer surface, wherein a translation handle is coupled to the outer surface and configured to move between the proximal end and the distal end; and
the instrument disposed within the tube and comprising a proximal end and a distal end, wherein the proximal end of the instrument is engaged with the translation handle and configured to move between a proximal position and a distal position, wherein in response to the translation handle moving to the distal end of the tube, the distal end of the instrument extends beyond the distal end of the tube;

wherein the translation handle facilitates movement of the instrument without direct contact between the translation handle and the instrument; and wherein the proximal end of the instrument comprises a coupler element positioned within the tube, with the translation handle compressing a portion of the tube in between the coupler element and the translation handle in a direction orthogonal to movement of the translation handle, and wherein the portion of the tube engages with the coupler element such that movement of the translation handle along the outer surface of the tube translates the distal end of the instrument between the retracted position and the advanced position.

10. The extension set of claim 9, wherein the instrument comprises a tubing.

11. The extension set of claim 9, wherein the fluid path assembly extends through the tube, wherein the instrument is configured to move with respect to the tube between a retracted position and an advanced position.

12. The extension set of claim 9, wherein the distal end of the tube comprises a distal connector.

13. The extension set of claim 12, wherein the distal end of the tube or the distal connector comprises a fluid seal to seal the tube.

14. The extension set of claim 9, wherein at least one of the coupler element and the tube comprises a lubricant to facilitate translation of the instrument within the tube.

15. The extension set of claim 9, wherein the translation handle comprises features formed thereon on opposing sides of the tube, the features comprising at least one of a roller, a low-friction sliding surface, and a bearing to provide localized compression of the tube to engage the coupler element through the tube, with the features having a radial distance therebetween that is less than an outer diameter of the tube.

16. A method to provide access to a patient's vascular system, comprising:
    coupling an extension set to a catheter assembly, wherein the extension set comprises:
        a tube, comprising a proximal end, a distal end, and an outer surface;
        an instrument disposed within the tube, the instrument comprising a proximal end and a distal end;
        a translation handle coupled to the outer surface of the tube, wherein the translation handle is configured to move along the outer surface of the tube between a proximal position and a distal position to translate the distal end of the instrument between a retracted position and an advanced position, wherein in response to the distal end of the instrument being in the advanced position, the distal end of the instrument extends beyond the distal end of the tube; and
        a coupler element provided at the proximal end of the instrument and positioned within the tube;
    wherein the translation handle facilitates moving of the instrument without direct contact between the translation handle and the instrument;
    wherein coupling the extension set to the catheter assembly comprises coupling the distal end of the tube to the catheter assembly;
    moving the translation handle along the tube from a proximal position to a distal position, wherein in response to the translation handle moving to the distal position, the distal end of the instrument extends beyond the distal end of the tube into the catheter assembly;
    wherein, as the translation handle is moved along the tube from the proximal position to the distal position, the translation handle mechanically pinches and compresses a portion of the tube in between the coupler element and the translation handle in a direction orthogonal to movement of the translation handle, with the portion of the tube engaging with the coupler element such that movement of the translation handle along the outer surface of the tube translates the distal end of the instrument between the retracted position and the advanced position.

17. The method of claim 16, wherein coupling the distal end of the tube to the catheter assembly comprises coupling a distal connector of the tube to one of a proximal end of the catheter assembly, a side port of the catheter assembly, and an adapter of the catheter assembly.

18. The method of claim 17, wherein the catheter assembly comprises a catheter extending from a distal end thereof, wherein in response to the translation handle moving to the distal position, the instrument extends through a distal end of the catheter.

19. The method of claim 18, wherein the extension set further comprises a blood collection device, further comprising after blood collection within the blood collection device, moving the translation handle from the distal position to the proximal position, wherein in response to moving the translation handle from the distal position to the proximal position, the distal end of the instrument is retracted into the tube.

20. The method of claim 18, wherein in moving the translation handle along the tube from the proximal position to the distal position, features formed on opposing sides of the translation handle longitudinally align with a flattened or concave center portion of the coupler element to facilitate engagement of the features with the coupler element through the tube, to smooth translation of the translation handle.

* * * * *